March 11, 1958 E. S. BOERNER Plant Pat. 1,688
ROSE PLANT
Filed Aug. 5, 1957
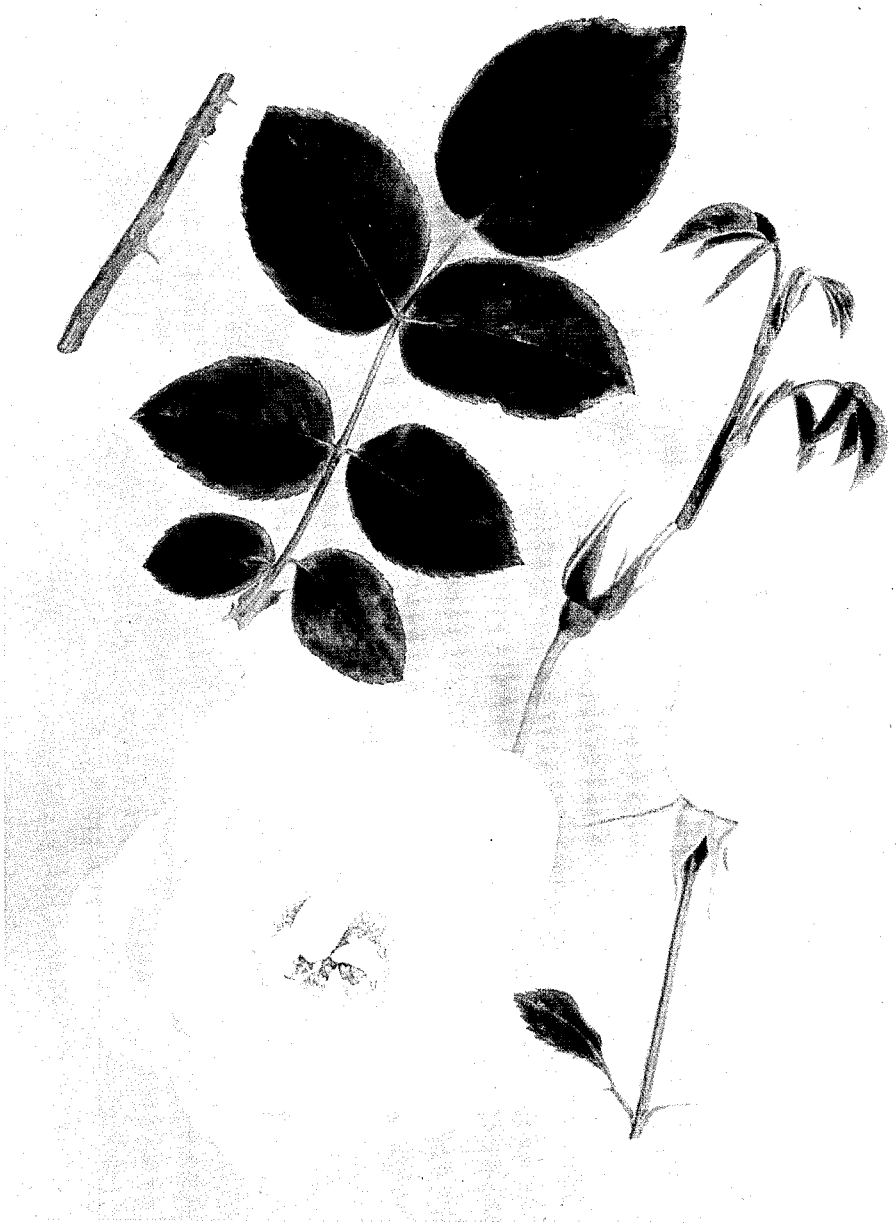
Inventor.
E. S. Boerner
By: Robb & Robb
Attorneys United States Patent Office Plant Pat. 1,688
Patented Mar. 11, 1958

1,688

ROSE PLANT

Eugene S. Boerner, Newark, N. Y., assignor to Jackson & Perkins Company, Newark, N. Y., a corporation of New York Application August 5, 1957, Serial No. 676,455

1 Claim. (Cl. 47—61)

The present invention relates to a new and distinct variety of rose plant of the large-flowered polyantha class, which was originated by me by crossing the variety "Sonata" (Plant Patent No. 732) with the variety "Fashion" (Plant Patent No. 789).

The primary objective of this cross was to produce a new variety of rose similar to the parent variety "Fashion," but having better shaped flowers. This objective was fully achieved, along with other desirable improvements, as evidenced by the following characteristics which are outstanding in the new variety and distinguish it from its parents, as well as from all other varieties of which I am aware:

(1) The pointed form of the buds;

(2) The large size and open form of the flowers;

(3) The rounded edges of the petals which are unusual in a rose;

(4) The White, lightly overcast with Marguerite Yellow general color tonality of the flowers; and (5) The Light Orange-Yellow stamens and Grenadine colored filaments, both forming a distinctive and attractive contrast to the background color of the flower petals.

Asexual reproduction of the new variety, by budding, as performed at Newark, New York and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.
*Seed parent.*—"Sonata."
*Pollen parent.*—"Fashion."

Classification:
*Botanic.*—Large-flowered polyantha.
*Commercial.*—Floribunda.

*Flower*

(Observations made from specimens grown outdoors at Newark, New York, near mid-afternoon in the latter part of June.)

Blooming habit: Recurrent—continuous.

Bud:
*Size.*—Medium.
*Form.*—Pointed; is not affected by wet or hot weather.
*Color.*—When sepals first divide—Marguerite Yellow, Plate 30, with edges lightly overcast with Chartreuse Yellow, Plate 31. When petals begin to unfurl—White, Plate 53, lightly overcast with Naphthalene Yellow, Plate 16. When halfblown: inside of petals—White, Plate 53, lightly overcast with Marguerite Yellow, Plate 30; reverse of petals—White, Plate 53, lightly overcast with Baryta Yellow, Plate 4 in the lower half of the petal.
*Sepals.*—Slightly branched; curl back when petals begin to unfurl. Color: inside—Pale Turtle Green, Plate 32; outside—Cress Green, Plate 31, lightly overcast with Carmine, Plate 1.
*Calyx.*—Color—Cress Green, Plate 31. Shape—pear. Size—small. Aspect—smooth. Odor when rubbed—none.
*Peduncle.* — Length — medium. Aspect — rough. Strength—erect; heavy. Color—Light Cress Green, Plate 31.
*Opening.*—Opens up well; is not affected by adverse weather conditions.

Bloom:
*Size.*—Large. Average size when fully expanded—from 3½ to 4 inches.
*Borne.*—Several together, and in irregular clusters.
*Stems.*—Medium length; strong.
*Form (when first open).*—Open. Permanence—retains its form to the end, but outer petals curl back.
*Petalage.*—Semi-double. Number of petals under normal conditions—from 30 to 35.
*Color.*—Center of flower—Marguerite Yellow, Plate 30, with lower half of petal lightly overcast with Pale Orange-Yellow, Plate 3. Outer petals—White, Plate 53, lightly overcast with Marguerite Yellow, Plate 30 in the lower half of the petal. Base of petals (aiglet)—Pale Greenish Yellow, Plate 5. Inside of petals—White, Plate 53, lightly overcast with Marguerite Yellow, Plate 30. Reverse of petals—White, Plate 53, lightly overcast with Sea-Foam Yellow, Plate 31 in the lower half of the petal. General tonality from a distance—White, Plate 53, lightly overcast with Marguerite Yellow, Plate 30.
*Discoloration.*—General tonality at end of first day—White, Plate 53, overcast with Marguerite Yellow, Plate 30. Second day—White, Plate 53, lightly overcast with Marguerite Yellow, Plate 30. Third day—White, Plate 53.

Petals:
*Texture.*—Leathery; is not affected by wet or hot weather.
*Appearance.*—Inside—satiny. Outside—shiny.
*Form.*—Round; slightly notched.
*Arrangement.*—Imbricated (regularly arranged shingle-like).
*Petaloids in center.*—Few; small.
*Persistence.*—Drop off cleanly.
*Fragrance.*—Strong. Nature—fresh tea.
*Lasting quality.*—On the plant—long. As cut flower—long.

*Genital organs*

Stamens, anthers: Medium size; many; regularly arranged around styles. Color—Light Orange-Yellow, Plate 3.
Stamens, filaments (threads): Long. Color—Grenadine, Plate 2.
Pollen: Color—Pale Yellow-Orange, Plate 3.
Styles: Bunched; uneven length; short, thin.
Stigmas: Color—Cream Color, Plate 16.
Ovaries: All enclosed in calyx.
Hips: None.
Seeds: None.

*Plant*

Form: Bush.
Growth: Vigorous; upright.
Foliage: Compound of 5 to 7 leaflets.
*Size.*—Large.
*Quantity.*—Normal.
*Color.*—New foliage: upper side—Yellowish Oil Green, Plate 5, lightly overcast with Bordeaux, Plate 12 on the outer edge of the leaf; under side—Bordeaux. Plate 12. Old foliage upper side—Varley's Green, Plate 18; under side—Light Cress Green, Plate 31.
*Shape.*—Oval.
*Texture.*—Upper side—leathery. Under side—smooth.
*Ribs and veins.*—Ordinary.
*Edge.*—Serrated (saw-toothed).
*Serration.*—Both double and single; small.
*Leaf stem.*—Color—Absinthe Green, Plate 31. Under side—smooth.
*Stipules.*—Long; smooth.
Wood:
*New wood.*—Color—Lettuce Green, Plate 5, lightly overcast with Acajou Red, Plate 13. Bark—smooth.

*Old wood.*—Color—Light Cress Green, Plate 31. Bark—smooth.
Thorns:
*Thorns.*—Quantity: on main stalks from base—ordinary; on laterals from stalk—ordinary. Form—flat base; medium length; straight. Color (when young)—Old Rose, Plate 13. Position—irregular.
*Prickles.*—Quantity: on main stalks—none; on laterals—none.
*Short needles.*—Quantity: on main stalk—none; on laterals—none.

I claim:

A new and distinct variety of rose plant of the large-flowered polyantha class, substantially as herein shown and described, characterized particularly as to novelty by the pointed form of its buds, the large size and open form of its flowers, the rounded edges of its flower petals, the White lightly overcast with Marguerite Yellow general color tonality of its flowers, the distinctive and contrasting Light Orange-Yellow color of the stamens, and the Grenadine color of the filaments of the flowers.

No references cited.